United States Patent [19]

Torelli

[11] Patent Number: 4,810,656

[45] Date of Patent: Mar. 7, 1989

[54] CHROMOGENIC REACTIVE FOR DETERMINING THE IRON CONTENT AND THE IRON-BINDING CAPACITY OF BIOLOGICAL LIQUIDS

[75] Inventor: Giorgio Torelli, Milan, Italy

[73] Assignee: Chemical Laboratories S.R.L., Milan, Italy

[21] Appl. No.: 947,133

[22] Filed: Dec. 29, 1986

[30] Foreign Application Priority Data

Dec. 27, 1985 [IT] Italy ................. 23396 A/85

[51] Int. Cl.$^4$ ................. G01N 33/20; G01N 33/49
[52] U.S. Cl. ................. 436/74; 436/84; 436/175; 436/910
[58] Field of Search ................. 436/66, 67, 74, 80, 436/175, 910, 84

[56] References Cited

U.S. PATENT DOCUMENTS

| | | | |
|---|---|---|---|
| 3,506,404 | 4/1970 | Evans et al. | 436/74 |
| 3,537,822 | 11/1970 | O'Malley et al. | 436/74 |
| 3,667,915 | 6/1972 | Klein | 436/74 |
| 3,898,042 | 8/1975 | Webb et al. | 436/80 |
| 4,092,117 | 5/1978 | Byrne | 436/80 |
| 4,224,034 | 9/1980 | Denney et al. | 436/74 |
| 4,308,027 | 12/1981 | Ceriotti | 436/74 |
| 4,407,962 | 10/1983 | Tabacco et al. | 436/74 |
| 4,567,150 | 1/1986 | Tabacco et al. | 436/84 |
| 4,588,695 | 5/1986 | Takano et al. | 436/74 |

FOREIGN PATENT DOCUMENTS

| | | | |
|---|---|---|---|
| 0061793 | 10/1982 | European Pat. Off. | 436/74 |
| 0137400 | 4/1985 | European Pat. Off. | 436/910 |
| 51-13039 | 4/1976 | Japan | 436/74 |

OTHER PUBLICATIONS

Tabacco et al., "Clin. Chim. Acta", 114; pp. 287–290, 1981.
Stephens et al., "Amer. Chem. Soc., Book and J. Div.", vol. 46, No. 6, pp. 692–696, May 1974.

*Primary Examiner*—Barry S. Richman
*Assistant Examiner*—Timothy M. McMahon
*Attorney, Agent, or Firm*—Guido Modiano; Albert Josif

[57] ABSTRACT

The present invention relates to a chromogenic reagent for determining the iron content and the iron-binding capacity of serum, comprising chromazurol B, a buffer for keeping the pH at 4.5–5, a surface-active substance in a concentration of at least 500 mg/l, a salt suitable for imparting an ionic strength expressed in terms of NaCl concentration of at least 100 g/l and an aminoacid suitable for selectively binding the Cu$^{2+}$ ions, in a concentration expressed in terms of glycine concentration ranging between 1 and 40 g/l.

6 Claims, 2 Drawing Sheets

CHROMOGENIC REACTIVE FOR DETERMINING THE IRON CONTENT AND THE IRON-BINDING CAPACITY OF BIOLOGICAL LIQUIDS

BACKGROUND OF THE INVENTION

The present invention relates to an improved reactive for determining the iron content and the overall iron-binding capacity of biological liquids, in particular of serum.

In 1979, Garcic in Clin. Chim. Acta. 94; 115–119 (1979), resuming a study carried out in 1969 by Shijo et al. in Jap. Analyst. (17); 1519–1523 (1968), devised a reagent for determining sideremia and the iron-binding capacity of serum (TIBC) containing the chromogenic chromazurol B (Cab) which, by reacting with iron, yields a compound with a high molar extinction at 630 nm ($A630 = 1.6 \times 10^5$ l/mol cm).

Subsequently, Tabacco et al. in 1981 in Clin. Chim. Acta. 114; 287–289 (1981), modified the reagent, replacing the sodium chloride with magnesium chloride, which allowed a greater recovery.

All these reagents were not free from disadvantages, which mainly lied in the interference of proteins and to a lesser extent in the presence of $Cu^{+2}$ in the serum, which biased the result of the analysis.

For this reason, the process employed with these reagents entailed the performing of blank sample, with obvious difficulties and disadvantages for the user.

In 1981, Brega, in the Italian patent application No. 20859 A/81, described a reagent, again containing the chromogenic chromazurol B, which was suitable for determining the iron and TIBC in the serum without a blank sample.

However, this reagent was also not free from the proteic and ionic interferences; the increase in color due to the interfering substances was simply compensated by the inability to extract and meter all the iron present in the serum.

Obviously these factors are variable, so that the reagent is inadequate to yield accurate results.

SUMMARY OF THE INVENTION

The object of the present invention is to provide an improved chromogenic reagent for determining the iron content and the iron-binding capacity of biological liquids, in particular of serum, suitable to eliminate the disadvantages of the similar reactives currently in use.

In particular, the specific aim of the present invention is to provide a chromogenic reagent as described above which eliminates the ionic and/or proteic interfering agents of the serum in the iron-chromogen reaction of the reagent.

This and other objects which will become apparent hereinafter are achieved by a chromogenic reagent for determining the iron content and the iron-binding capacity of serum, comprising a chromogen composed of chromazurol B (CAB), a surface-active substance and a buffer for keeping the pH of the reactive at 4.5–5, characterized in that it comprises at least one salt in an amount suitable to impart to the reagent an ionic strength, expressed in terms of NaCl concentration, of at least 100 g/l.

According to a preferred embodiment of the reagent according to the invention, the same comprises said surface-active substance in a concentration higher than 500 mg/l.

According to an even more advantageous embodiment of the reagent according to the present invention, it jointly comprises said surface-active substance in a concentration of at least 500 mg/l, at least one salt for an ionic strength expressed in terms of NaCl concentration of at least 100 g/l and furthermore comprises at least one aminoacid or a derivative thereof suitable for selectively binding the $Cu^{2+}$ in an amount equal to a glycine concentration ranging between 1 and 40 g/l.

It has been observed that the use of a high ionic strength and/or of an increased concentration of surface-active substance in the reagent according to the invention lead to the elimination of the proteic interferences in the iron-CAB chromogen reaction. Without being bound to any theoretical interpretation, it seems that the increase in the concentration of the surface-active substance renders the chromogenic substance more finely dissolved and decreases its availability for reaction with proteins. Furthermore, the increase of the ionic strength causes a shift in the absorption spectrum of the chromogen such that, in the useful readout range of the spectrum, the increase in color due to the CAB-protein reaction is compensated by the reduction of the color due to the decrease of the CAB in solution.

On the other hand, it has been observed that the use of an aminoacid or of a derivative thereof capable of binding $Cu^{2+}$, but not $Fe^{3+}$, in the indicated concentration, leads to the formation of a complex with the copper ion, thus no longer making it available for reaction with the CAB.

These effects, which can be achieved with the reagent according to the invention, are better illustrated in the accompanying drawings, where:

DESCRIPTION OF THE PREFERRED EMBODIMENTS

Figure 1:
FIG. 1 is a colorimetric absorption spectra of a serum sample to which the chromogenic reagent of the present invention has been added and of a control sample.

FIG. 1 illustrates the colorimetric absorption spectrum of CAB to which an aminoacid has been added, according to the present invention, and in contact with a serum containing copper ions (lower curve) in comparison with the spectrum of the CAB without aminoacid in contact with an identical serum containing the above said ions (upper curve).

Figure 2:
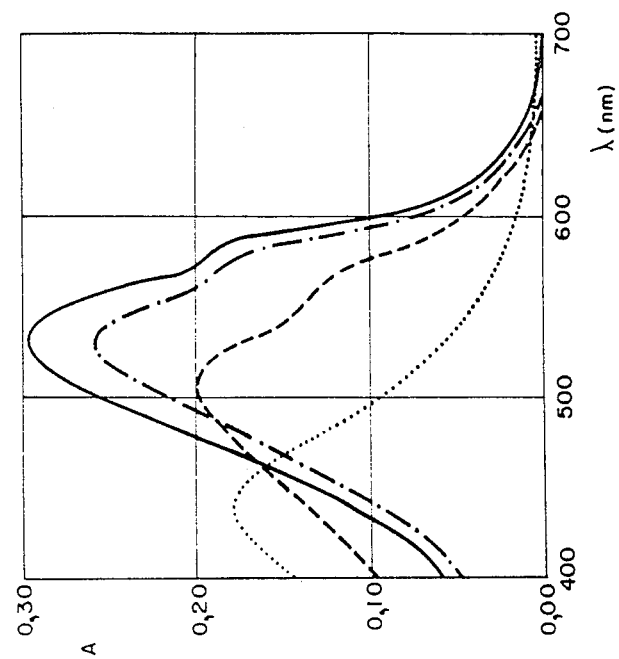
FIGS. 2 and 3 illustrate absorption spectra of chromogenic reagents reacted with interfering proteins.

From FIG. 2, it can be seen that in the reagent without aminoacid the chromogen has reacted with the $Cu^{2+}$ ions of the sample yielding the strongly interfering colored compound the spectrum of which is depicted by the upper curve.

FIG. 2 illustrates absorption spectra of chromogenic reagents which have reacted with interfering proteins, of which the continuous curve relates to the reagent according to the present invention, the dot-and-dash curve relates to a reagent with a halved concentration of surface-active substance, the broken line curve relates to a reagent with the ionic strength reduced to one third and the dotted curve relates to a reagent without surface-active substance.

The proteic interferences examined in this figure have been studied by precipitating in the serum, with EDTA (100–150 mg/ml) the ions (among which iron, too) which react with the chromogen.

From FIG. 2, it can be seen that the surface-active substance, by dissolving the chromogen more finely, alters the structure thereof, while the increase in the ionic strength determines a rightward shift of the absorption maximum.

FIG. 3 again illustrates absorption spectra of reagents which have reacted with interfering proteins, of which the continuous curve is related to the reagent according to the invention, the dot-and-dash curve relates to the same reagent with a halved concentration of surface-active substance, the broken line curve relates to the reagent according to the invention but with the ionic strength reduced to one third and the dotted curve relates to the same reagent without CAB.

Figure 3:
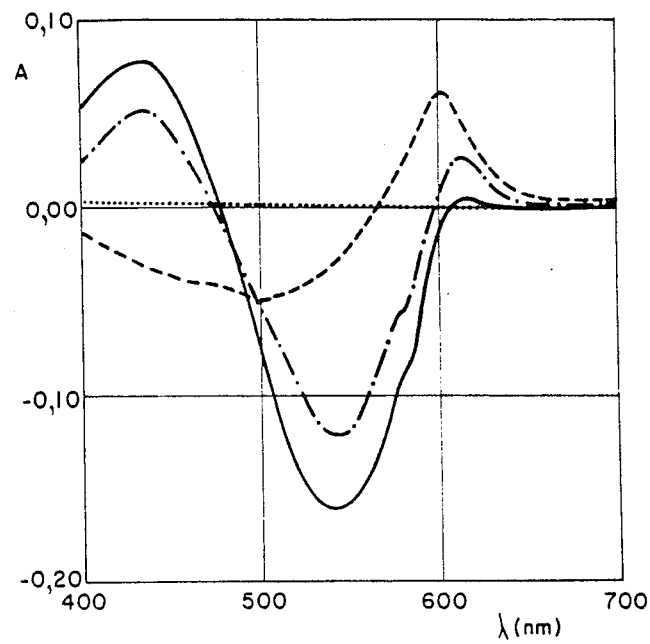

From FIG. 3 it can be seen that the chromogen-protein reaction determines a spectrum with three peaks, two positive ones and a negative one therebetween, which are the algebraic sum of the color which forms from the reaction itself minus the color which disappears due to the decrease of CAB in the reagent. Of these three peaks, only the rightmost positive one yields interferences in the readouts in the useful interval of $\lambda = 610$–$650$ nm and therefore errors. Therefore, it must be eliminated.

The originality of the research which has led to the present invention lies in that it has shown that, by significantly increasing the concentration of the surface-active substance, the protein-CAB interactions decrease.

Furthermore, by shifting the negative peak rightwards as the ionic strength increases, the rightmost positive peak disappears.

It has thus been found that with a reagent according to the invention there are no interferences at $\lambda$ greater than 610 nm and the absorptions, in the range of $0.004 \pm 0.002$, are fully comparable to those which are obtained on sera treated with reagent without CAB and therefore are negligible as far as analysis is concerned.

Accordingly (see FIG. 4), at lengths greater than 610 nm, the spectrum on the standard has the same pattern as the spectrum on the sera, and therefore the calculated values of iron concentration remain constant as $\lambda$ varies.

Figure 4:
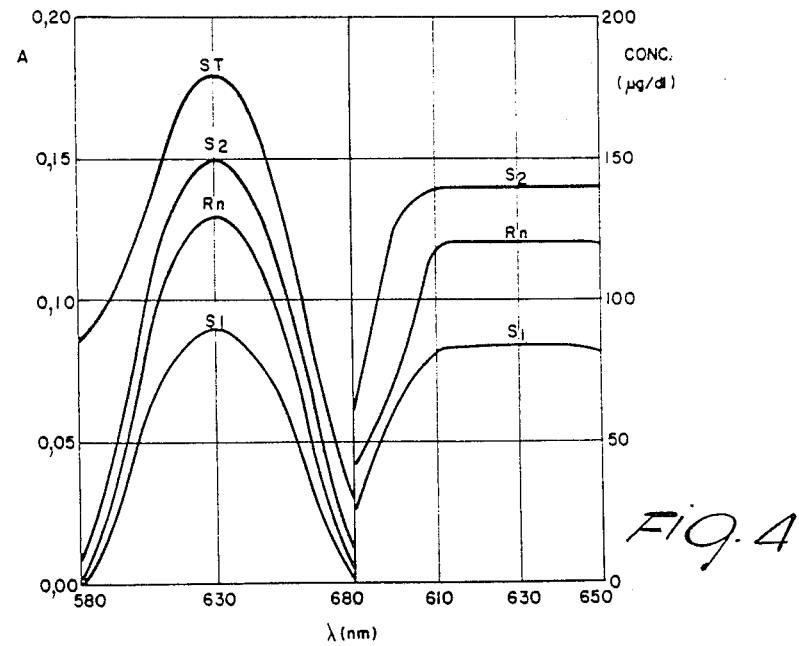
FIG. 4 illustrates absorption spectra on a standard (St), on a control serum (Rn) and on two human test sera ($S_1$ and $S_2$).

This is illustrated in FIG. 4 which depicts, to the left, the absorption spectra on a standard (St) (consisting of a $Fe^{3+} 30$ Mmol/l solution), on a control serum (Rn) (consisting of Control serum Roche) and on two human test sera ($S_1$ and $S_2$). The same FIG. 4, to the right, illustrates the values of serum iron concentration calculated with the formula:

$$C = \text{Standard value} \times \frac{A \text{ of sample}}{A \text{ of standard}}$$

The chromogen used in the reagent according to the present invention is ex conc. BN azure dichrome (C.I. mordant blue 1/4380) commonly termed chromazurol B (CAB). A quantity of chromogen is used which may vary between 40 to 80 mg per liter of reagent.

The surface-active substance which can be used in the reagent according to the invention may be any one commonly used in similar analytical reagents.

As an example, it is possible to use cetyltrimethylammonium bromide (CTMA), Triton X100 produced by B. D. H. and composed of isooctylphenoxypolyethoxyethanol, Therit produced by CARL Klinke and composed of hydroxypolyethoxydodecane, or ethylhexadecyldimethylammonium bromide by KODAK, of which the first, i.e. CTMA, is preferred.

The salt which may be used to impart the ionic strength required in the reagent according to the invention may be any. Obviously, for reasons of availability and cost, NaCl is preferred.

The ionic strength of the reagent is calculated, as is known, according to the formula $$M = \tfrac{1}{2}[\text{anions conc.} \times \text{anions valence}^2 + \text{cations conc.} \times \text{cations valence}^2]$$

The aminoacid preferably used in the reagent according to the invention is glycine or its derivative glycylglycine, glycylalanine, but it is equally possible to use other aminoacids such as alanine, glutamic acid, etc., or a derivative thereof containing said aminoacids in its structure.

The reagent according to the invention may be prepared by means of conventional methods by purifying CAB, salifying it with the amount of salt suitable to impart the abovementioned ionic strength thereto, and mixing it with the surface-active substance, the aminoacid and an appropriate buffer suitable to keep the pH at 4.5–5, e.g. a buffer of acetic acid-sodium acetate.

The following example illustrates a method of preparing the reagent according to the invention.

EXAMPLE

| | |
|---|---|
| Chromazurol B | 65 mg |
| Sodium acetate | 32 g |
| Magnesium chloride | 108 g |
| Acetic acid | 8 ml |
| CTMA | 1 g |
| 25% ammonia | 50 ml |
| Glycine | 7.5 g |

The whole is dissolved into one liter of distilled $H_2O$.

The reagent thus obtained is useful in determining the concentration of iron and the iron-binding capacity of serum with the conventional colorimetric methods, without the use of blank sample.

Thus, in the determination of the iron, the sample of serum, a standard and a blank composed of distilled water are mixed with an equal amount of reagent, and after accurate agitation of the mixture the readout is performed of the absorption of the sample and of the standard against the blank, at 630 nm. Then the iron concentration is calculated with the formula described above in relation to FIG. 4.

In order to determine the total iron-binding capacity, the sample of serum is saturated with an iron saturation agent, then left to react after accurate agitation, the excess iron is removed by absorption on carbon dust and subsequent centrifugation and the iron present in the supernatant is metered with the same process used above to determine the iron.

From what has been described, it can be seen that the reagent according to the invention achieves the intended objects, constituting a safe and reliable means of analysis which eliminates the ionic and proteic interferences and allows to achieve accurate and reproducible analysis results.

I claim:

1. A method for determining the iron content and the iron-binding capacity of serum comprising the steps of:
   providing a chromogenic reagent comprising chromazurol B (CAB) chromogen, a surface-active substance and a buffer for maintaining the pH of the reagent at 4.5–5, wherein said surface-active substance has a concentration higher than 500 mg/l and said reagent further comprises at least one salt in an amount to impart to the reagent an ionic strength, expressed in terms of NaCl concentration, of at least 100 g/l, and at least one aminoacid selected from the group consisting of glycine, glycylglycine, glycylalanine, alanine, glutamic acid, and derivatives thereof suitable to form a complex with $Cu^{2+}$ but not with $Fe^{3+}$, in an amount having a copper ion binding capacity corresponding to that of glycine when used in a concentration ranging of from 1 to 40 g/l;
   contacting a sample of serum with said chromogenic reagent;
   measuring the colorimetric absorption spectrum of the sample thus treated, and;
   correlating the measured absorption spectrum to the iron content and iron-binding capacity of the sample by a predetermined correlation.

2. A chromogenic reagent for determining the iron content and the iron-binding capacity of serum, comprising chromazurol B (CAB) chromogen, a surface-active substance and a buffer for maintaining the pH of the reagent at 4.5–5, wherein said surface-active substance has a concentration higher than 500 mg/l and said reagent further comprises at least one salt in an amount to impart to the reagent an ionic strength, expressed in terms of NaCl concentration, of at least 100 g/l, and at least one aminoacid selected from the group consisting of glycine, glycylglycine, glycylalanine, alanine, glutamic acid, and derivatives thereof suitable to form a complex with $Cu^{2+}$ but not with $Fe^{3+}$, in an amount having a copper ion binding capacity corresponding to that of glycine when used in a concentration ranging of from 1 to 40 g/l.

3. A chromogenic reagent according to claim 2 comprising chromazurol B in a concentration of 40–80 mg/l.

4. A chromogenic reagent according to claim 2 wherein said surface-active substance is selected from the group consisting of cetyltrimethylammonium bromide, isooctylphenoxypolyethoxyethanol, hydroxypolyethoxydodecane and ethylhexadecyldimethylammonium bromide.

5. A chromogenic reagent according to claim 2 wherein said aminoacid is selected from the group consisting of glycine, glycylglycine, alanine, glycylalaine and glutamic acid.

6. A chromogenic reagent according to claim 5 wherein said aminoacid is glycine.

* * * * *